US 11,701,014 B2

United States Patent
Kawamura et al.

(10) Patent No.: US 11,701,014 B2
(45) Date of Patent: Jul. 18, 2023

(54) VALVE, GAS CONTROL DEVICE, AND SPHYGMOMANOMETER

(71) Applicant: Murata Manufacturing Co., Ltd., Kyoto (JP)

(72) Inventors: Kenichiro Kawamura, Kyoto (JP); Yukiharu Kodama, Kyoto (JP); Kosuke Narita, Kyoto (JP); Hiroki Achiwa, Kyoto (JP); Hiroshi Takemura, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 587 days.

(21) Appl. No.: 16/118,959

(22) Filed: Aug. 31, 2018

(65) Prior Publication Data

US 2018/0368704 A1 Dec. 27, 2018

Related U.S. Application Data

(63) Continuation of application No. PCT/JP2017/026021, filed on Jul. 19, 2017, and a (Continued)

(30) Foreign Application Priority Data

Jul. 29, 2016 (JP) ................... 2016-150123

(51) Int. Cl.
*A61B 5/0235* (2006.01)
*A61B 5/0225* (2006.01)
(Continued)

(52) U.S. Cl.
CPC .......... *A61B 5/0235* (2013.01); *A61B 5/0225* (2013.01); *A61B 5/02233* (2013.01); (Continued)

(58) Field of Classification Search
None
See application file for complete search history.

(56) References Cited

U.S. PATENT DOCUMENTS 8,526,651 B2 * 9/2013 Lafort ................. H04R 25/604
381/328
2005/0047934 A1 3/2005 Nawa
(Continued)

FOREIGN PATENT DOCUMENTS

JP 2005-076534 A 3/2005
TW 200507802 A 3/2005
(Continued)

OTHER PUBLICATIONS

International Search Report for International Application No. PCT/JP2017/021898, dated Aug. 22, 2017.
(Continued)

*Primary Examiner* — Jacqueline Cheng
*Assistant Examiner* — Jairo H Portillo
(74) *Attorney, Agent, or Firm* — Pearne & Gordon LLP

(57) ABSTRACT

A gas control device includes a pump, a valve, a cuff, and a controller. The valve includes a first plate having a first vent hole and a first vent hole, a channel forming plate having an exhaust hole and an exhaust channel, a second plate having a second vent hole, and an edge separation plate. A manchette rubber tube in the cuff is joined to the periphery of the second vent hole in the second plate by an adhesive, and thus the valve is connected to the cuff. The exhaust hole is opened to the atmosphere. The pump includes a pump housing having a discharge hole and a discharge hole. The upper surface of the pump housing is joined to the bottom surface of the edge separation plate.

20 Claims, 11 Drawing Sheets

Related U.S. Application Data continuation of application No. PCT/JP2017/021898, filed on Jun. 14, 2017.

(51) Int. Cl.

| | | |
|---|---|---|
| *F16K 7/17* | (2006.01) | |
| *A61B 5/022* | (2006.01) | |
| *F04B 45/047* | (2006.01) | |
| *F16K 7/00* | (2006.01) | |

(52) U.S. Cl.
CPC .............. *F04B 45/047* (2013.01); *F16K 7/00* (2013.01); *F16K 7/17* (2013.01)

(56) References Cited

U.S. PATENT DOCUMENTS

| | | | |
|---|---|---|---|
| 2005/0047940 A1 | 3/2005 | Nawa | |
| 2006/0147329 A1* | 7/2006 | Tanner | F04B 43/046 |
| | | | 417/505 |
| 2008/0290312 A1* | 11/2008 | Hirose | F16K 7/14 |
| | | | 251/333 |
| 2013/0178752 A1 | 7/2013 | Kodama et al. | |
| 2015/0034847 A1 | 2/2015 | Kotani et al. | |
| 2017/0215744 A1 | 8/2017 | Kawamura | |

FOREIGN PATENT DOCUMENTS

| | | |
|---|---|---|
| WO | 2012/141113 A1 | 10/2012 |
| WO | 2013/157304 A1 | 10/2013 |
| WO | 2016/063710 A1 | 4/2016 |

OTHER PUBLICATIONS

International Search Report for International Application No. PCT/JP2017/026021, dated Sep. 19, 2017.
Written Opinion for International Application No. PCT/JP2017/021898, dated Aug. 22, 2017.
Written Opinion for International Application No. PCT/JP2017/026021, dated Sep. 19, 2017.

* cited by examiner

VALVE, GAS CONTROL DEVICE, AND SPHYGMOMANOMETER

This application is a continuation of International Application No. PCT/JP2017/021898 filed on Jun. 14, 2017 which claims priority from Japanese Patent Application No. 2016-150123 filed on Jul. 29, 2016. This application is also a continuation of International Application No. PCT/JP2017/026021 filed Jul. 19, 2017 which also claims priority from Japanese Patent Application No. 2016-150123 filed on Jul. 29, 2016. The contents of these applications are incorporated herein by reference in their entireties.

FIELD OF THE DISCLOSURE

Embodiments of the present disclosure relate to a valve that adjusts a gas flow, a gas control device, and a sphygmomanometer.

DESCRIPTION OF THE RELATED ART

Various gas control devices for controlling a gas flow have been invented. One example gas control device including a piezoelectric pump, a valve, and a cuff is disclosed in Patent Document 1. The piezoelectric pump has a suction hole and a discharge hole. The valve includes a first plate having a first vent hole and a second plate having a second vent hole and an exhaust hole. The second plate has a nozzle, and the inside of the nozzle forms the second vent hole. The discharge hole in the piezoelectric pump is connected to the first vent hole in the valve. The cuff is attached to the nozzle in the valve. The second vent hole in the valve is connected to the cuff.

Patent Document 1: International Publication No. 2016-63710

BRIEF SUMMARY OF THE DISCLOSURE

In recent years, a reduction in profile has been required for the gas control device in Patent Document 1 from the viewpoint of usability. One approach to this need is removing the nozzle for the reduction in profile and joining the cuff directly to the periphery of the second vent hole in the second plate. This approach needs to have a wide joining area for joining the cuff in the second plate.

Unfortunately, however, the second plate has the exhaust hole, and the second plate may be unable to have a region for firmly joining the cuff. Therefore, the second plate is not allowed to have the wide joining area. Accordingly, the gas control device in Patent Document 1 has a problem in that it is difficult to join the large container capable of holding a large quantity of air directly to the second plate.

It is an object according to embodiments of the present disclosure to provide a valve, a gas control device, and a sphygmomanometer that can achieve a reduction in profile and can have a wide joining area.

A valve according to embodiments of the present disclosure includes a first plate having a first vent hole, a second plate having a second vent hole, a channel forming plate joined to the first plate and the second plate and having an exhaust hole, a first channel connecting the first vent hole and the second vent hole, a second channel connecting the second vent hole and the exhaust hole, and a valve member forming a first valve chamber with the first plate and the channel forming plate and forming a second valve chamber with the second plate and the channel forming plate, the valve member connecting the first channel and interrupting the second channel or interrupting the first channel and connecting the second channel on the basis of a pressure of the first valve chamber and a pressure of the second valve chamber.

In this configuration, the exhaust hole is provided to the channel forming plate. Thus, the second plate can have a wide joining area. The joining area is an area for joining a container.

Accordingly, the valve according to embodiments of the present disclosure can achieve a reduction in profile and can have a wide joining area.

A gas control device according to embodiments of the present disclosure includes the valve according to embodiments of the present disclosure, a pump, and a container. The pump has a discharge hole connected to the first vent hole. The container is connected to the second vent hole. The exhaust hole is opened to the atmosphere.

Because the gas control device according to embodiments of the present disclosure includes the valve according to embodiments of the present disclosure, substantially the same advantages as those in the valve in the present disclosure are obtainable.

A sphygmomanometer according to embodiments of the present disclosure includes the gas control device according to embodiments of the present disclosure.

Because the sphygmomanometer according to embodiments of the present disclosure includes the valve according to embodiments of the present disclosure, substantially the same advantages as those in the valve in the present disclosure are obtainable.

The valve according to embodiments of the present disclosure can achieve a reduction in profile and can have a wide joining area.

DETAILED DESCRIPTION OF THE DISCLOSURE

A gas control device 100 according to a first embodiment of the present disclosure is described below.

Figure 1:
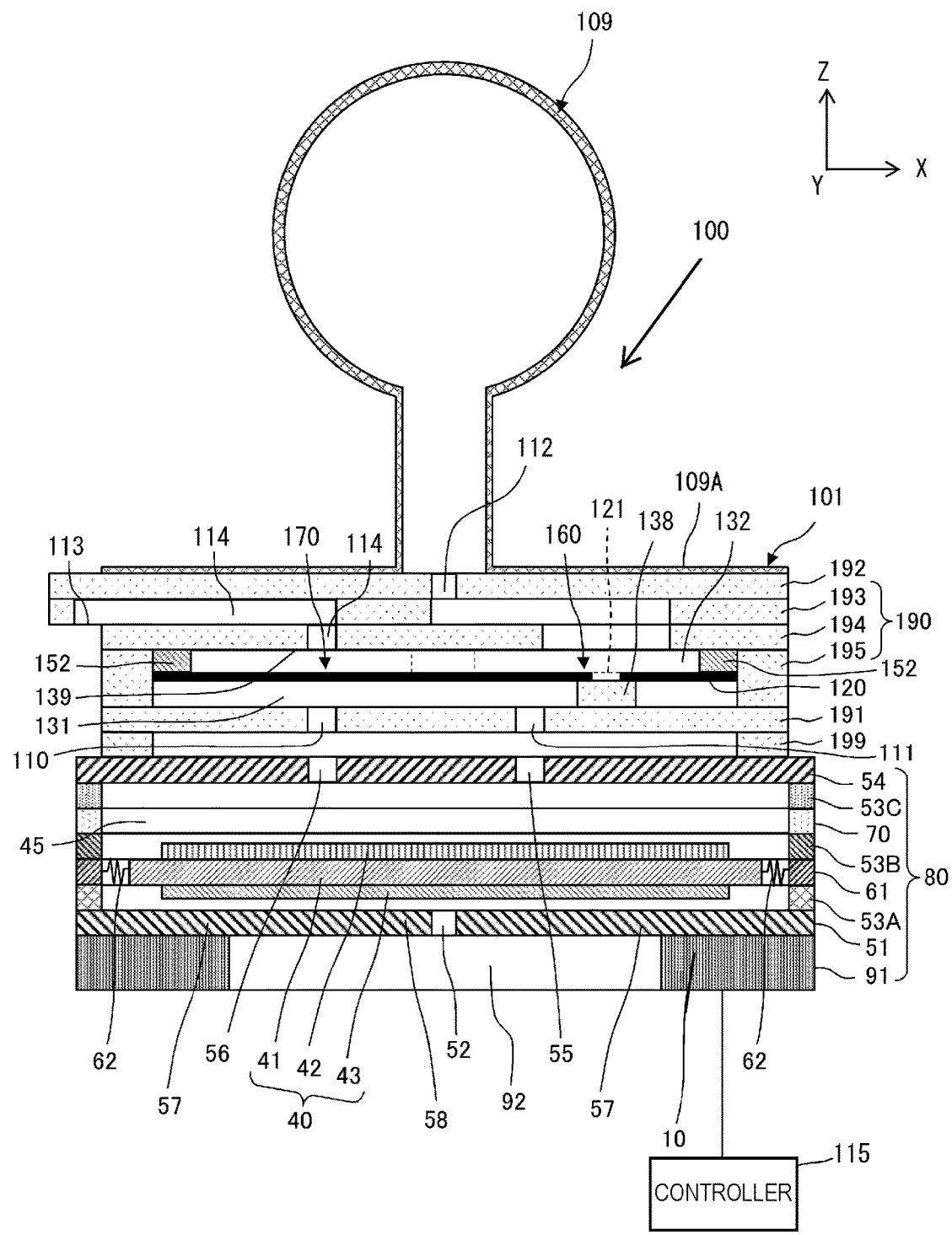
FIG. 1 is a cross-sectional view of a main portion of a gas control device 100 according to a first embodiment of the present disclosure.

FIG. 1 is a cross-sectional view of a main portion of the gas control device 100 according to the first embodiment of the present disclosure. The gas control device 100 includes a pump 10, a valve 101, a cuff 109, and a controller 115. One example of the gas control device 100 is included in a sphygmomanometer for measuring a blood pressure of a subject.

The valve 101 includes a first plate 191 having first vent holes 110 and 111, a channel forming plate 190 having an exhaust hole 113 and an exhaust channel 114, a second plate 192 having a second vent hole 112, and an edge separation plate 199. The channel forming plate 190 is composed of an intermediate plate 194, an exhaust channel forming plate 193, and a frame plate 195.

The valve 101 constitutes a check valve 160 and an exhaust valve 170. A manchette rubber tube 109A in the cuff 109 is joined to the periphery of the second vent hole 112 in the second plate 192 by an adhesive, and thus the valve 101 is connected to the cuff 109. The exhaust hole 113 is open to the atmosphere.

The pump 10 includes a pump housing 80 having discharge holes 55 and 56. The upper surface of the pump housing 80 is joined to the bottom surface of the edge separation plate 199 in the valve 101. Thus, the first vent holes 110 and 111 in the valve 101 are connected to the discharge holes 55 and 56 in the pump 10.

One example of the controller 115 includes a microcomputer and controls the operations of the units in the gas control device 100. The controller 115 is connected to the pump 10 and transmits a control signal to the pump 10. The controller 115 produces an alternating-current driving voltage from a commercial alternating-current power supply, applies it to the pump 10, and drives the pump 10. Then, the controller 115 measures a blood pressure based on the pressure of air held in the cuff 109. A value of the pressure of the air held in the cuff 109 is detected by a pressure sensor (not illustrated), and the detected value is input into the controller 115.

The cuff 109 corresponds to one example of a "container" in the present disclosure.

Here, the structure of each of the pump 10 and valve 101 is described. First, the structure of the pump 10 is described with reference to FIGS. 1 and 2.

Figure 2:
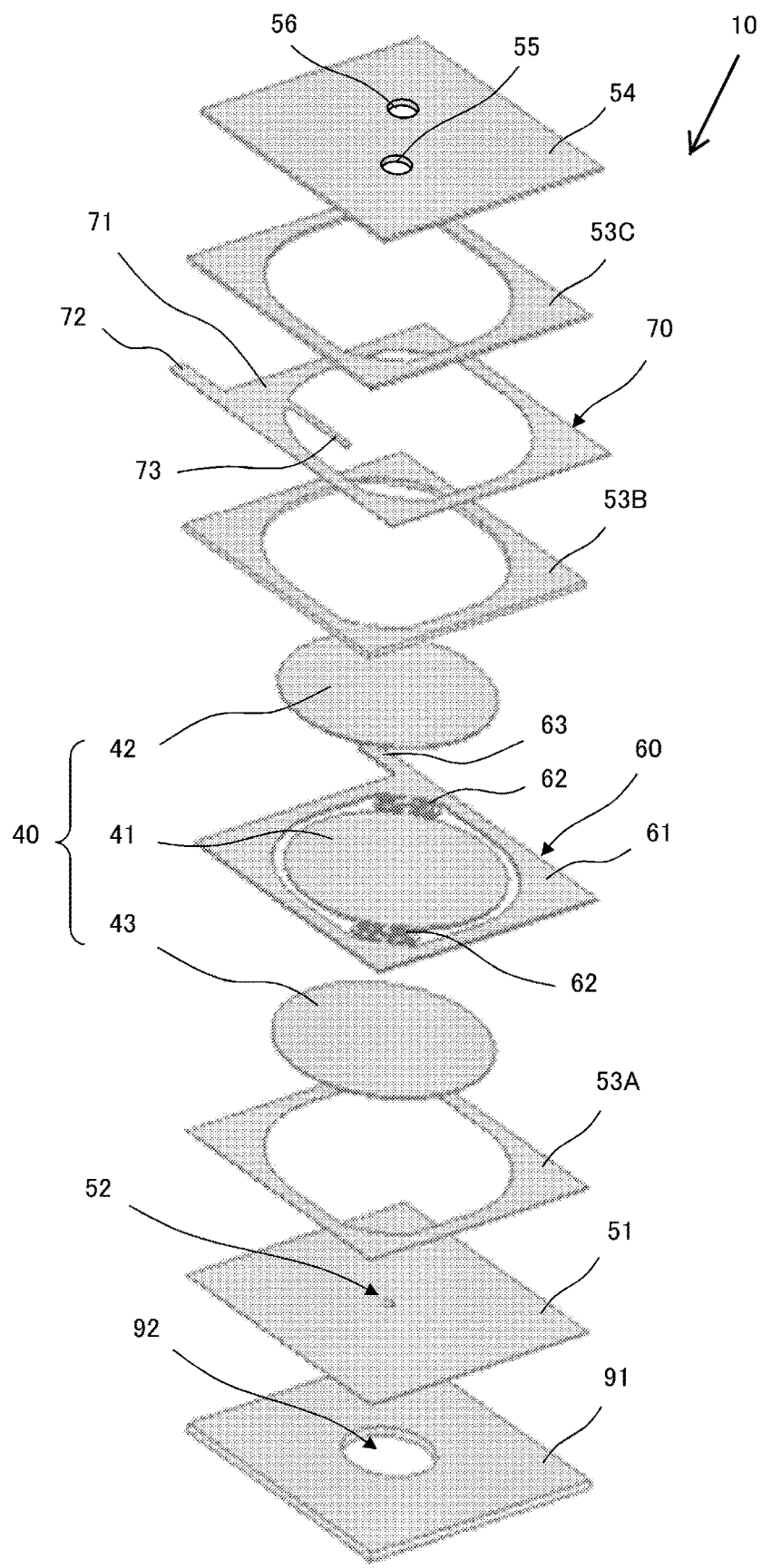
FIG. 2 is an exploded perspective view of a pump 10 illustrated in FIG. 1.

FIG. 2 is an exploded perspective view of the pump 10 illustrated in FIG. 1. The pump 10 includes a substrate 91, a flexible plate 51, a spacer 53A, a reinforcing plate 43, a vibration plate unit 60, a piezoelectric element 42, a spacer 53B, an electrode conduction plate 70, a spacer 53C, and a lid plate 54, and has a structure in which they are laminated in order.

The substrate 91, flexible plate 51, spacer 53A, a section of the vibration plate unit 60, spacer 53B, electrode conduction plate 70, spacer 53C, and lid plate 54 constitute the pump housing 80. The inner space of the pump housing 80 corresponds to a pump chamber 45. One example material of the pump housing 80 is a metal.

The vibration plate unit 60 is composed of a vibration plate 41, a frame plate 61, coupling portions 62, and an outer terminal 63. The vibration plate unit 60 is formed by performing the punching processing on a metal plate.

The frame plate 61 is positioned around the vibration plate 41. The outer terminal 63 for electrical connection is disposed on the frame plate 61. The vibration plate 41 is coupled to the frame plate 61 with the coupling portions 62. One example shape of the coupling portions 62 is a narrow ring. The coupling portions 62 have an elastic structure with elasticity of a small spring constant.

Accordingly, the vibration plate 41 is elastically supported at two points on the frame plate 61 in a flexible manner with the two coupling portions 62. Thus, bending and vibrating of the vibration plate 41 is not substantially hindered. That is, a piezoelectric actuator 40 is in a state in which its peripheral portion (as well as central portion) is not practically locked.

The piezoelectric element 42 is disposed on the upper surface of the disc-shaped vibration plate 41. The reinforcing plate 43 is disposed on the lower surface of the vibration plate 41. The vibration plate 41, piezoelectric element 42, and reinforcing plate 43 constitute the disc-shaped piezoelectric actuator 40. One example of the piezoelectric element 42 may be made of a PZT-based ceramic material.

The vibration plate 41 may be formed from a metal plate having a higher coefficient of linear expansion than that of each of the piezoelectric element 42 and reinforcing plate 43 by heating and curing it at the time of bonding. This formation can avoid warping of the entire piezoelectric actuator 40, can make an appropriate compressive stress remain in the piezoelectric element 42, and can prevent the breakage of the piezoelectric element 42.

For example, the vibration plate 41 may be made of a material having a high coefficient of linear expansion, such as phosphor bronze (C5210) or stainless steel SUS301, and the reinforcing plate 43 may be made of a material such as a 42 nickel, 36 nickel, or stainless steel SUS430.

As for the vibration plate 41, piezoelectric element 42, and reinforcing plate 43, the piezoelectric element 42, reinforcing plate 43, and vibration plate 41 may be arranged in this order from the above. In this case, by setting a material of each of the reinforcing plate 43 and vibration plate 41 so as to make an appropriate compressive stress remain in the piezoelectric element 42, the coefficient of linear expansion is adjusted.

The spacer 53B is disposed on the upper surface of the frame plate 61. The spacer 53B is made of a resin. The spacer 53B has a thickness equal to or slightly larger than that of the piezoelectric element 42. The frame plate 61 electrically isolates the electrode conduction plate 70 and vibration plate unit 60 from each other.

The electrode conduction plate 70 is disposed on the upper surface of the spacer 53B. The electrode conduction plate 70 is made of a metal. The electrode conduction plate 70 includes a frame portion 71 having a substantially circular opening, an internal terminal 73 projecting into the opening, and an outer terminal 72 projecting outward.

The leading end of the internal terminal 73 is joined to the surface of the piezoelectric element 42 by soldering. By setting the position where they are joined together by soldering at the position corresponding to the node of bending and vibrating of the piezoelectric actuator 40, the vibration of the internal terminal 73 is suppressed.

The spacer 53C is disposed on the upper surface of the electrode conduction plate 70. The spacer 53C is made of a resin. The spacer 53C has a thickness substantially equal to that of the piezoelectric element 42. The spacer 53C is a spacer for preventing the solder portion of the internal terminal 73 from coming into contact with the lid plate 54 while the piezoelectric actuator 40 is vibrating. It also prevents a decrease in the vibration amplitude caused by air resistance produced by an excessive approach of the surface of the piezoelectric element 42 to the lid plate 54. Thus, the thickness of the spacer 53C is substantially equal to that of the piezoelectric element 42. The lid plate 54 is disposed on the upper surface of the spacer 53C. The lid plate 54 has the discharge holes 55 and 56. The lid plate 54 covers the upper portion of the piezoelectric actuator 40.

The spacer 53A is disposed on the lower surface of the vibration plate unit 60. The spacer 53A is positioned between the upper surface of the flexible plate 51 and the lower surface of the vibration plate unit 60. The spacer 53A has the thickness in which approximately several tens of micrometers is added to the thickness of the reinforcing plate 43. The spacer 53A is a spacer for preventing the piezoelectric actuator 40 from coming into contact with the flexible plate 51 while the piezoelectric actuator 40 is vibrating. The flexible plate 51 is disposed on the lower surface of the spacer 53A. The flexible plate 51 has a suction hole 52 at its center.

The substrate 91 is disposed on the lower surface of the flexible plate 51. The substrate 91 has a cylindrical cavity 92 at its central portion. The flexible plate 51 includes a fixed portion 57 fixed to the substrate 91 and a movable portion 58 positioned nearer the center than the fixed portion 57 and facing the cavity 92.

The movable portion 58 can vibrate at virtually the same frequency as that of the piezoelectric actuator 40 because of the pressure fluctuations of the air resulting from the vibration of the piezoelectric actuator 40. The natural frequency of the movable portion 58 is designed to be the same as or slightly lower than the driving frequency of the piezoelectric actuator 40.

When the flexible plate 51 is designed to have a vibration phase lagging behind the vibration phase of the piezoelectric actuator 40 (for example, with a lag of 180 degrees), the thickness fluctuations of the gap between the flexible plate 51 and piezoelectric actuator 40 practically increase.

Accordingly, when an alternating-current driving voltage is applied on the outer terminals 63 and 72 by the controller 115, the piezoelectric actuator 40 bends and vibrates concentrically. In addition, together with the vibration of the piezoelectric actuator 40, the movable portion 58 in the flexible plate 51 also vibrates. Thus, the pump 10 sucks air through the cavity 92 and suction hole 52 into the pump chamber 45. Then, the pump 10 discharges the air from the pump chamber 45 through the discharge holes 55 and 56. The suction hole 52 and discharge holes 55 and 56 communicate with each other at all times.

At this time, in the pump 10, the peripheral portion of the piezoelectric actuator 40 is not practically fixed. Thus, according to the pump 10, losses produced with the vibration of the piezoelectric actuator 40 are small, and a high discharge pressure and a large discharge flow rate are obtainable even with a small and low-profile structure.

Next, the relation between a temperature and a maximum discharge pressure of the pump 10 is described.

When the pump 10 having the piezoelectric element 42 as a driving source keeps being driven, the temperature of the pump 10 keeps increasing because of self-heating. It is known that when the temperature of the pump 10 keeps increasing, the discharge performance of the pump 10 decreases.

The heat source of the self-heating is the piezoelectric actuator 40. The pump housing 80 is made of a metal having a high conductivity. Thus, the heat of the piezoelectric actuator 40 is quickly conducted to the pump housing 80 through the coupling portions 62.

Next, the structure of the valve 101 is described with reference to FIGS. 1 and 3.

Figure 3:
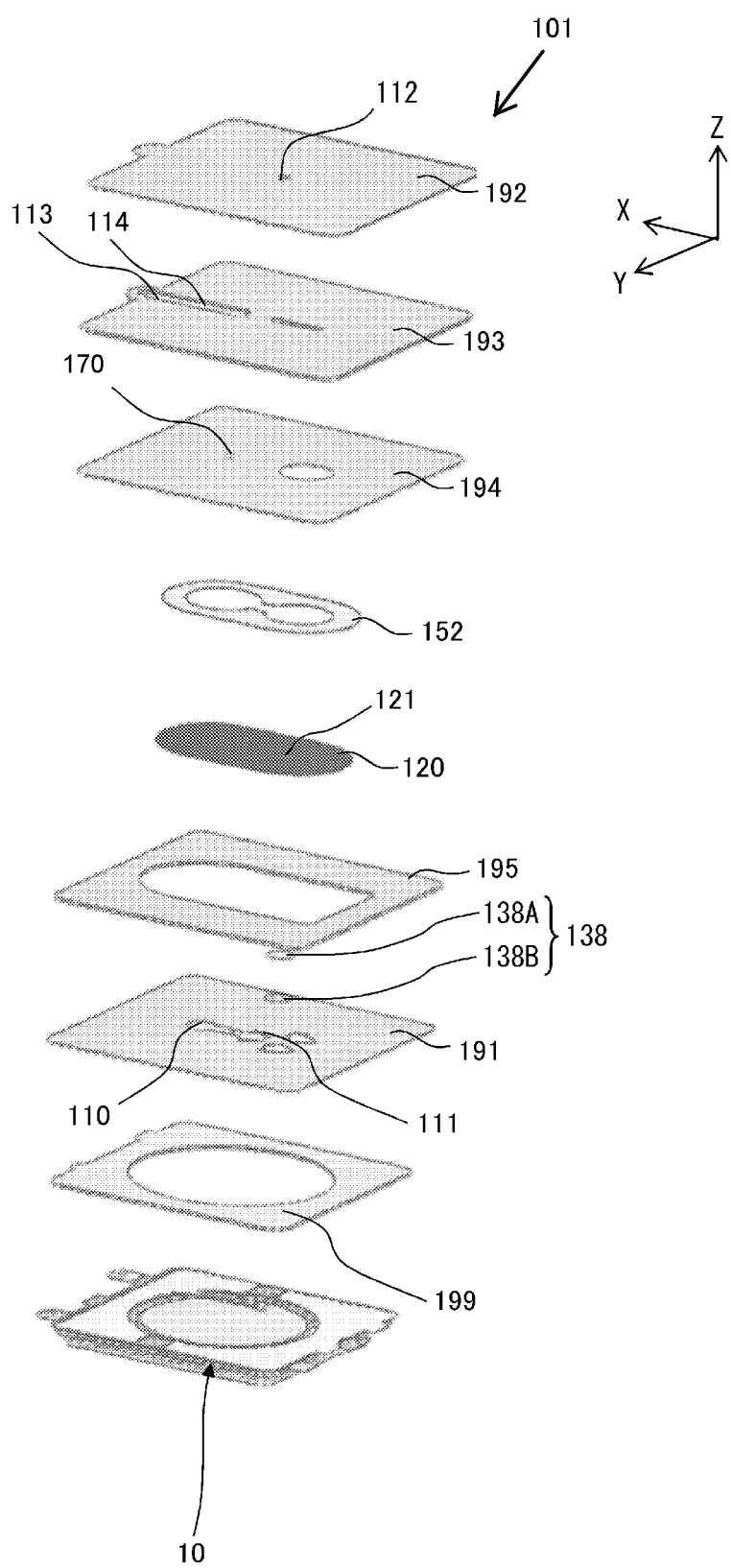
FIG. 3 is an exploded perspective view of a valve 101 illustrated in FIG. 1.

FIG. 3 is an exploded perspective view of the valve 101 illustrated in FIG. 1. In FIG. 3, the Z-axis direction, Y-axis direction, and X-axis direction are illustrated. The Z-axis direction indicates the direction in which the members constituting the valve 101 are laminated. The X-axis direction indicates the direction in which the check valve 160 and exhaust valve 170 are arranged. The Y-axis direction indicates the direction perpendicular to the Z-axis direction and X-axis direction.

The valve 101 includes the edge separation plate 199, the first plate 191 having the first vent holes 110 and 111, the frame plate 195, a diaphragm 120 formed from a rectangular thin film, a sealing member 152 formed from a rectangular thin film, the exhaust channel forming plate 193, the intermediate plate 194, and the second plate 192 having the second vent hole 112, as illustrated in FIGS. 1 and 3, and has a structure in which they are laminated in sequence. Thus, the inner surface of the second plate 192 (second principal surface of the second plate in the present disclosure), exhaust channel forming plate 193, and intermediate plate 194 form the exhaust channel 114. Therefore, the thickness of the valve 101 can be reduced. The diaphragm 120 and sealing member 152 are disposed in an opened region in the frame plate 195.

The second vent hole 112 is a through hole in the second plate 192. Accordingly, the opening of the second vent hole 112 is flush with (lies in substantially the same plane of) the outer surface of the second plate 192 (first principal surface of the second plate in the present disclosure).

The exhaust channel forming plate 193, intermediate plate 194, and frame plate 195 constitute the channel forming portion 190. One side surface of the exhaust channel forming plate 193 protrudes in part. The exhaust channel forming plate 193, intermediate plate 194, and frame plate 195 are laminated such that their respective side surfaces are flush with each other, except for the protruding portion of the exhaust channel forming plate 193.

The exhaust channel forming plate 193 has a slit for forming the exhaust channel 114 together with the second plate 192 and intermediate plate 194. A first end of the slit reaches the protruding portion of the side surface. The opened portion of the slit near the second plate 192 is covered with the second plate 192. The exhaust channel forming plate has a through hole in a position different from that of the above-described slit. The through hole constitutes a section of a first channel.

Because the exhaust channel forming plate 193 and intermediate plate 194 are arranged in the above-described relationship, the opened portion of the slit near the intermediate plate 194 is covered with the intermediate plate 194, except for the first end and a second end. Accordingly, the first end of the slit in the exhaust channel forming plate 193 is opened to the side near the intermediate plate 194. This opened portion is the exhaust hole 113. Thus, the exhaust hole 113 is disposed in a side surface of the valve 101 and has a shape opened to the side near the pump 10. That is, the opening of the exhaust hole 113 faces the side near the pump 10. The exhaust hole 113 is not opened in the surface of the second plate 192, that is, the surface to which the cuff 109 is attached.

The intermediate plate 194 has a through hole in a portion opposed to the second end of the slit in the exhaust channel forming plate 193, and this through hole opposed to the second end communicates with the second valve chamber 132. The slit and through hole form the exhaust channel 114 in an in-plane direction of the second plate 192. That is, the exhaust channel 114 can be formed of the second principal surface of the second plate 192, whose first principal surface forms the top surface of the valve 101. Accordingly, the exhaust channel 114 in the in-plane direction can be formed, and the thickness of the valve 101 can be reduced. The intermediate plate has another through hole different from the above-described through hole. The different through hole forms a section of the first channel.

The frame plate 195 forms an inner space together with the second plate 192 and first plate 191. The diaphragm 120 is positioned in the inner space.

One example material of the edge separation plate 199 may be a PET resin. One example material of each of the first plate 191, channel forming plate 190, and second plate 192 may be a metal. Each of the joints between the second plate 192, intermediate plate 193, exhaust channel forming plate 194, frame plate 195, and first plate 191 may be formed by double-faced tape, thermal diffusion joining, an adhesive, or the like.

The diaphragm 120 constitutes one example of a "valve member" in the present disclosure.

The second plate 192 has the second vent hole 112 communicating with the cuff 109 and a valve seat 139 positioned around the exhaust channel 114 leading to the exhaust hole 113, as illustrated in FIGS. 1 and 3. One example of the second plate 192 may be made of a resin.

The first plate 191 has the first vent hole 110 communicating with the discharge hole 56 in the pump 10 and the first vent hole 111 communicating with the discharge hole 55 in the pump 10, as illustrated in FIGS. 1 and 3. One example of the first plate 191 may be made of a metal.

The diaphragm 120 has a circular hole portion 121 at its central portion in an area opposed to a valve seat 138, as illustrated in FIGS. 1 and 3. The hole portion 121 has a diameter smaller than that of the surface of the valve seat 138 being in contact with the diaphragm 120. The perimeter of the diaphragm 120 is smaller than that of each of the first plate 191 and second plate 192. One example of the diaphragm 120 may be made of rubber, such as ethylene propylene diene monomer (EPDM) rubber or silicone rubber.

The diaphragm 120 is held between the first plate 191 and exhaust channel forming plate 194 with the sealing member 152 interposed therebetween. Thus, a section of the diaphragm 120 is in contact with the valve seat 139, and the periphery of the hole portion 121 in the diaphragm 120 is in contact with the valve seat 138. The valve seat 138 is disposed on the first plate 191 so as to press the periphery of the hole portion 121 in the diaphragm 120. The valve seat 138 includes protrusion portions 138A and 138B. One example material of each of the protrusion portions 138A and 138B may be a metal.

The diaphragm 120 divides the inner space defined by the second plate 192, first plate 191, and frame plate 195. The region in the inner space near the first plate 191 is a first valve chamber (first chamber) 131, and the region in the inner space near the second plate 192 is a second valve chamber (second chamber) 132. One example diameter of each of a first valve chamber 131 and a second valve chamber 132 may be 7.0 mm. One example diameter of the surface of the valve seat 138 being in contact with the diaphragm 120 may be 1.5 mm.

In the valve 101, a section of the sealing member 152 is positioned inside the second valve chamber 132. Examples of the sealing member 152 may include double-faced tape and an adhesive.

Next, the check valve 160 and exhaust valve 170 constituted by the valve 101 are described.

First, the check valve 160 is composed of the periphery of the hole portion 121 in the diaphragm 120 and the valve seat 138 coming into contact with that periphery and covering the hole portion 121. In the check valve 160, the diaphragm 120 comes into contact with or becomes separated from the valve seat 138 on the basis of the pressure of the first valve chamber 131 and the pressure of the second valve chamber 132.

Second, the exhaust valve 170 is composed of a section of the diaphragm 120 and the valve seat 139 positioned around the exhaust channel 114. In the exhaust valve 170, the section of the diaphragm 120 comes into contact with or becomes separated from the valve seat 139 on the basis of the pressure of the first valve chamber 131 and the pressure of the second valve chamber 132. Here, a portion with which the section of the diaphragm 120 comes into contact is referred to as the valve seat 139.

Next, operations of the gas control device 100 during a blood pressure measurement are described.

Figure 4:
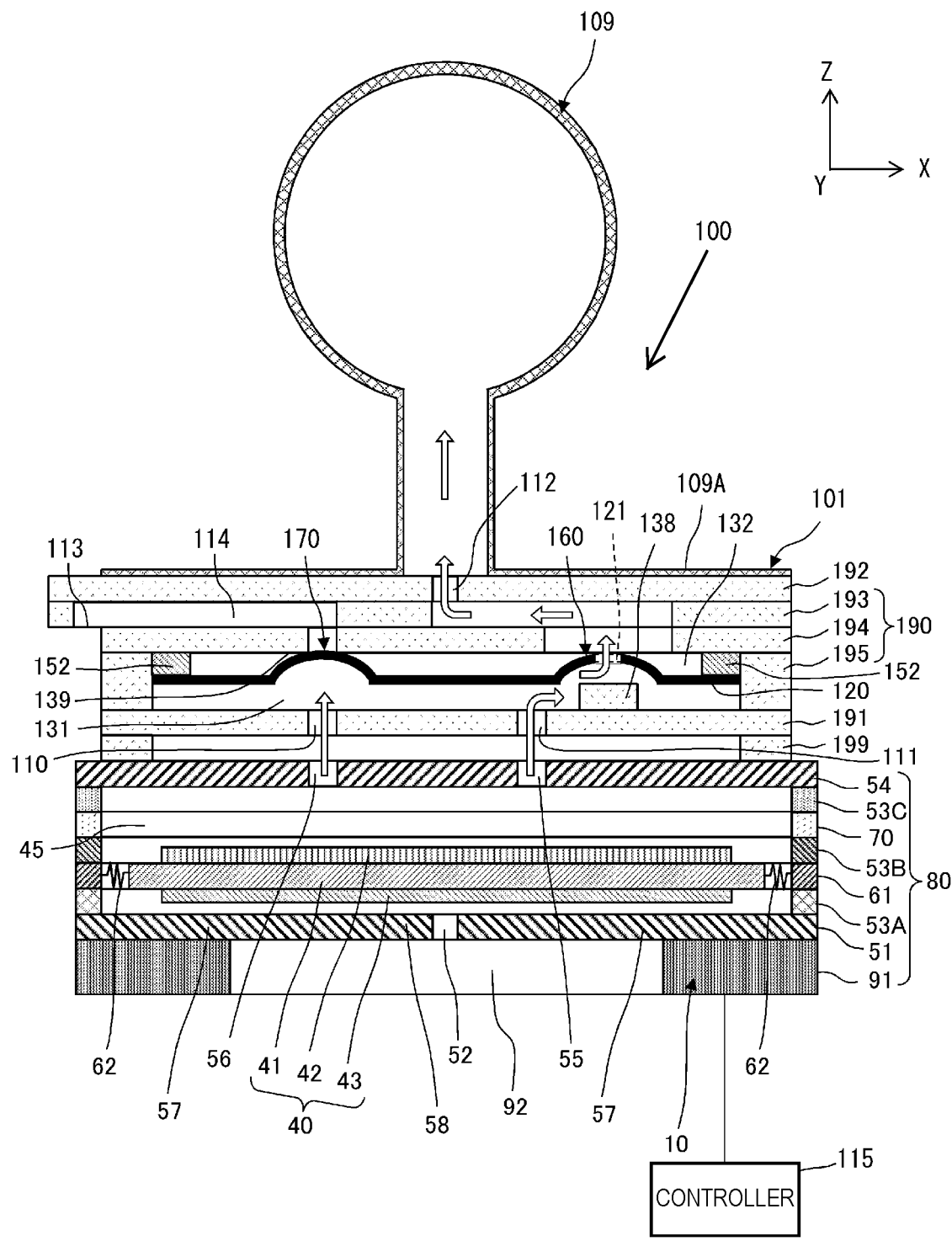
FIG. 4 is a schematic diagram that illustrates an air stream in the gas control device 100 while the pump 10 illustrated in FIG. 1 is driven.

FIG. 4 is a schematic diagram that illustrates an air stream in the gas control device 100 while the pump 10 illustrated in FIG. 1 is driven. The controller 115 activates the pump 10 at the time of starting a blood pressure measurement. When the pump 10 is driven, first, air flows through the cavity 92 and suction hole 52 into the pump chamber 45 in the pump 10. Then, the air is discharged through the discharge hole 55 and discharge hole 56 and flows into the first valve chamber 131 in the valve 101.

In the exhaust valve 170, the pressure of the first valve chamber 131 becomes higher than that of the second valve chamber 132. Thus, as illustrated in FIG. 4, the diaphragm 120 seals the exhaust channel 114 and interrupts the linkage between the second vent hole 112 and exhaust channel 114.

In the check valve 160, the pressure of the first valve chamber 131 becomes higher than that of the second valve chamber 132. Thus, the periphery of the hole portion 121 in the diaphragm 120 becomes separated from the valve seat 138, and the first vent hole 111 and second vent hole 112 become linked to each other with the hole portion 121 interposed therebetween. The channel bridging the first vent hole 111 and second vent hole 112 corresponds to a first channel in the present disclosure.

Accordingly, air is sent from the pump 10 to the cuff 109 through the first vent hole 111, hole portion 121, and second vent hole 112 in the valve 101 (see FIG. 4), and the pressure (air pressure) inside the cuff 109 increases. While the pump 10 is driven, the temperature of the pump 10 keeps rising because of self-heating.

The diaphragm 120 is fixed to the second plate 192 and first plate 191 such that the periphery of the hole portion 121 in the diaphragm 120 can come into contact with the valve seat 138. The valve seat 138 pressurizes the periphery of the hole portion 121 in the diaphragm 120.

The air moving through the first vent hole 111 in the valve 101 and out of the hole portion 121 flows into the second valve chamber 132 with a pressure slightly lower than the discharge pressure of the pump 10. The discharge pressure of the pump 10 is placed on the first valve chamber 131.

Accordingly, in the valve 101, the pressure of the first valve chamber 131 becomes slightly higher than that of the second valve chamber 132, and the state in which the diaphragm 120 seals the exhaust channel 114 and the hole portion 121 is opened is maintained.

Figure 5:
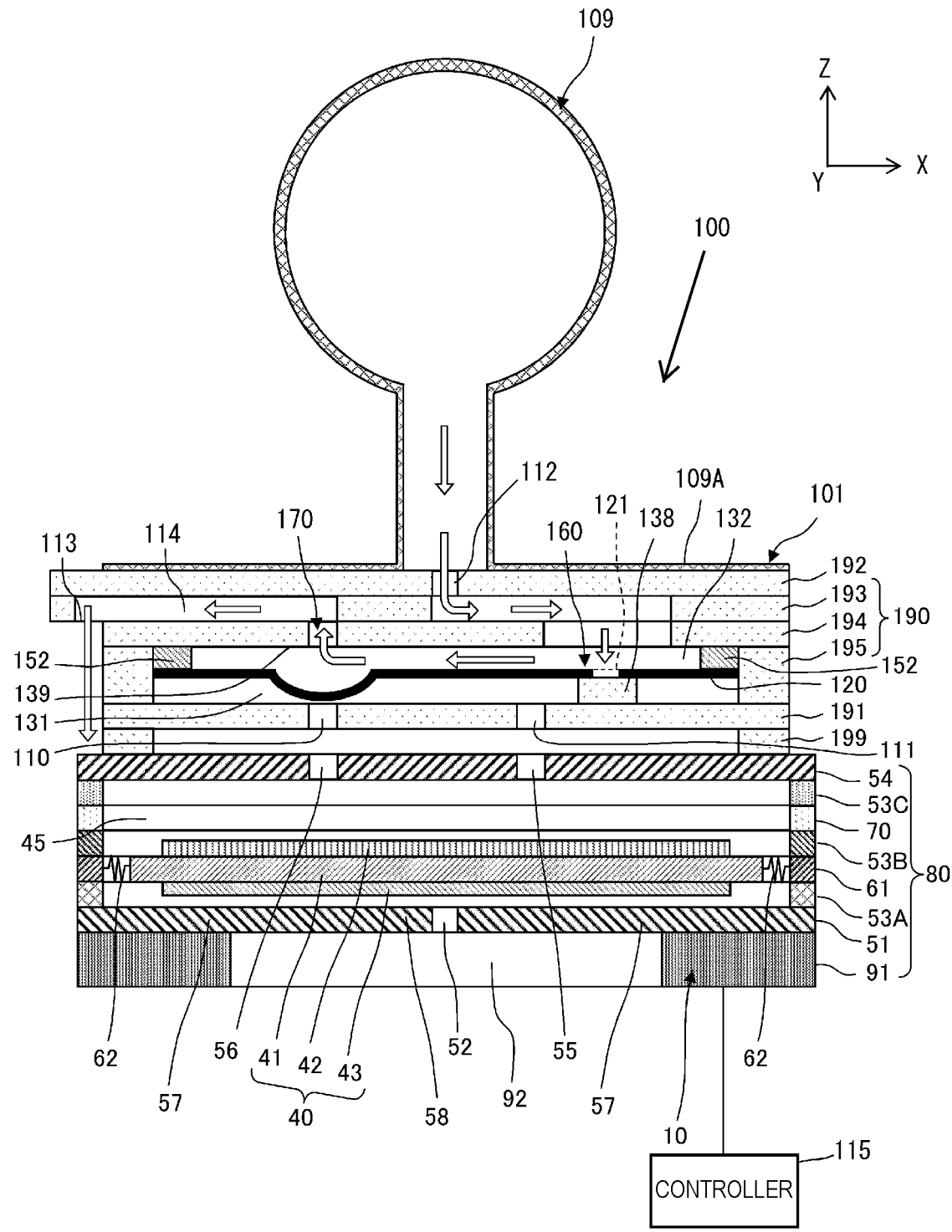
FIG. 5 is a schematic diagram that illustrates an air stream in the gas control device 100 immediately after the pump 10 illustrated in FIG. 1 stops being driven.

FIG. 5 is a schematic diagram that illustrates an air stream in the gas control device 100 immediately after the pump 10 illustrated in FIG. 1 stops being driven. When the blood pressure measurement ends, the controller 115 deactivates the pump 10. When the driving of the pump 10 stops, the air is promptly ejected from the pump chamber 45 and first valve chamber 131 to outside the gas control device 100 through the suction hole 52 and cavity 92 in the pump 10. The pressure of the cuff 109 is placed on the second valve chamber 132 through the second vent hole 112 interposed therebetween.

Accordingly, in the check valve 160, the pressure of the first valve chamber 131 becomes lower than that of the second valve chamber 132. The diaphragm 120 comes into contact with the valve seat 138 and seals the hole portion 121. In the exhaust valve 170, the pressure of the first valve chamber 131 becomes lower than that of the second valve chamber 132. The diaphragm 120 becomes separated from the valve seat 139 and opens the exhaust channel 114. That is, in the valve 101, the second vent hole 112 and exhaust channel 114 become linked to each other with the second valve chamber 132 interposed therebetween. Because the exhaust hole 113 is opened to the side near the pump housing 80, as described above, the air inside the cuff 109 moves through the second vent hole 112, second valve chamber 132, and exhaust channel 114 and is quickly ejected from the exhaust hole 113 toward the pump housing 80. The channel bridging the second vent hole 112 and exhaust hole 113 corresponds to a second channel in the present disclosure. The volume of the air held in the cuff 109 is significantly higher than that of the pump 10, and a large amount of air is ejected from the exhaust hole 113 toward the pump housing 80.

Consequently, the gas control device 100 can cool the pump housing 80 without a dedicated heat sink or dedicated cooler and can suppress a temperature rise in the pump 10. Therefore, the gas control device 100 can cool the pump 10 without using a cooler even with a low-profile structure.

After that, the controller 115 activates the pump 10 at the time of starting a blood pressure measurement and deactivates the pump 10 when the blood pressure measurement ends. In this manner, for multiple blood pressure measurements, the gas control device 100 can cool the pump 10 every time a blood pressure measurement ends.

In the above-described configuration, the exhaust hole 113 is opened from the exhaust channel forming plate 193 to the side near the intermediate plate 194 and is not opened in the surface of the second plate 192. Thus, the second plate 192 can have a wide joining area. The joining area is an area for joining the manchette rubber tube 109A in the cuff 109.

Accordingly, the valve 101 and gas control device 100 can achieve a reduction in profile and can have a wide joining area.

As previously described, in the valve 101, a section of the sealing member 152 is positioned inside the second valve chamber 132. Thus, the sealing member 152 can bond the first plate 191, second plate 192, and diaphragm 120 and can also catch the foreign matter inside each of the valve chambers 131 and 132. Accordingly, if the foreign matter enters the valve 101, malfunctions caused by the foreign matter can be suppressed. In particular, in the exhaust valve 170, blockages in the exhaust hole 113 or exhaust channel 114 caused by foreign matter can be suppressed.

A gas control device according to a second embodiment of the present disclosure is described below.

Figure 6:
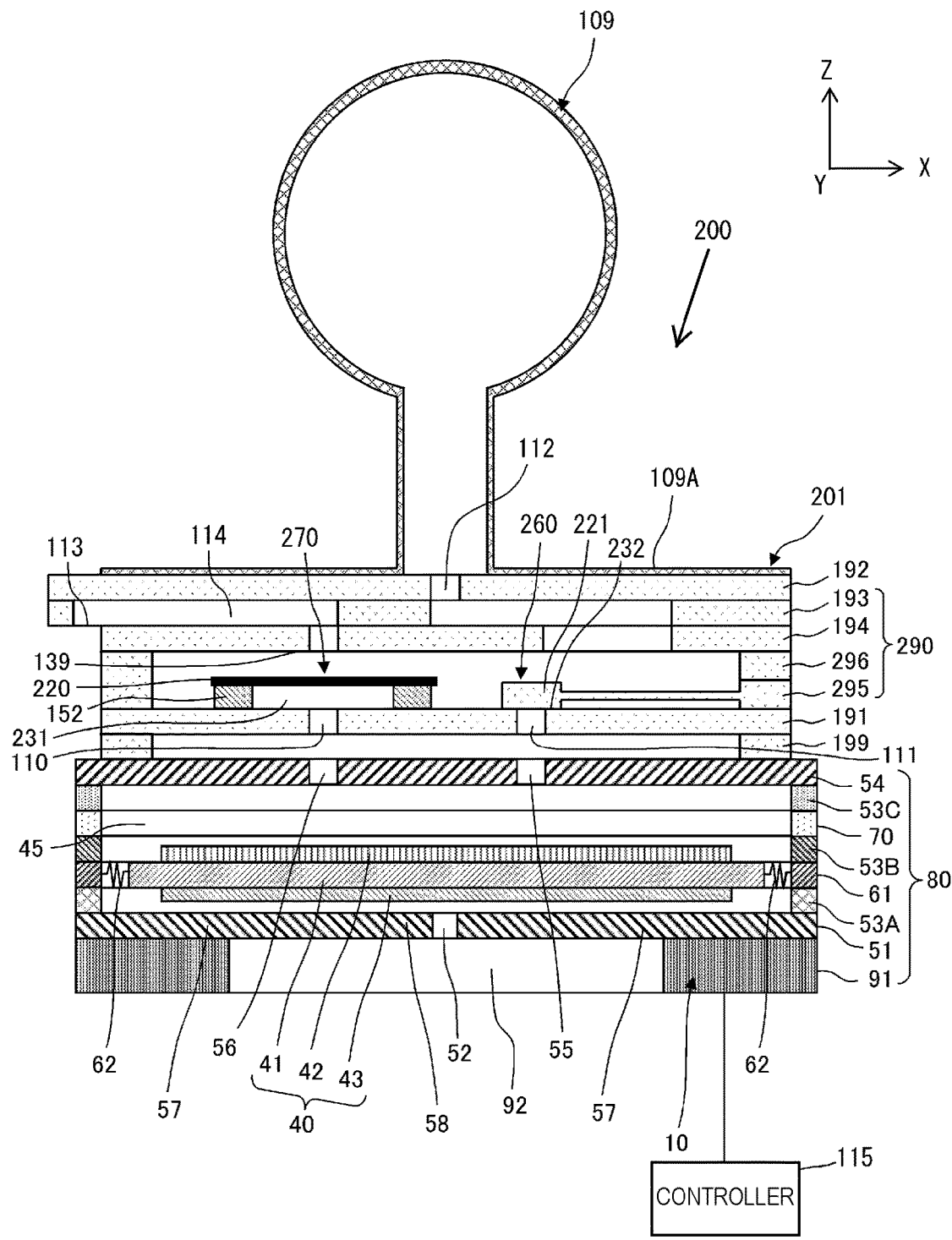
FIG. 6 is a cross-sectional view of a main portion of a gas control device 200 according to a second embodiment of the present disclosure.
Figure 7:
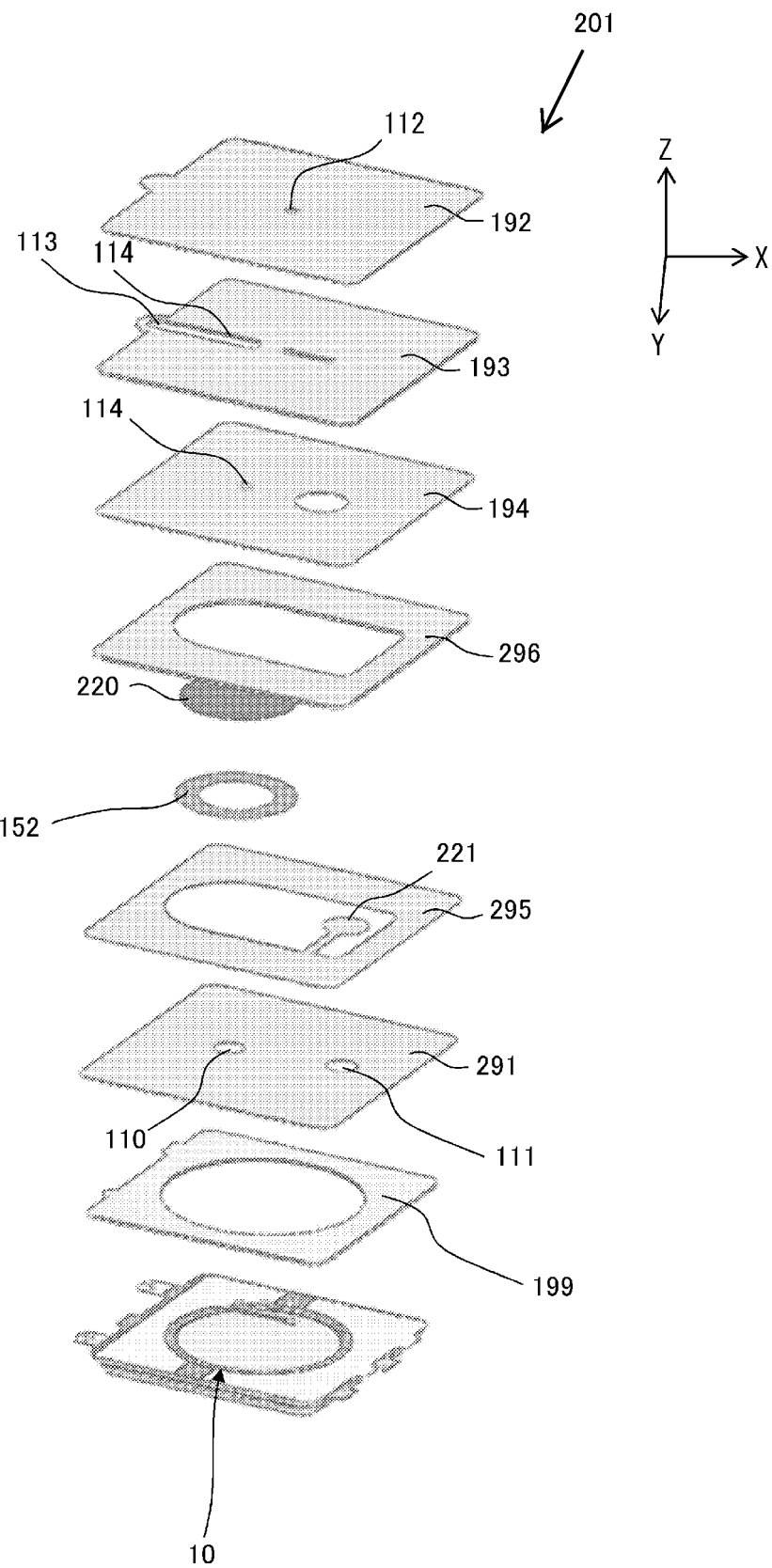
FIG. 7 is an exploded perspective view of a valve 201 illustrated in FIG. 6.

FIG. 6 is a cross-sectional view of a main portion of a gas control device 200 according to the second embodiment of the present disclosure. FIG. 7 is an exploded perspective view of a valve 201 illustrated in FIG. 6. The gas control device 200 in the second embodiment differs from the gas control device 100 in the first embodiment in that it includes a channel forming plate 290 including a frame plate 296 and a non-return plate 295. The channel forming plate 290 differs from the channel forming plate 190 in the first embodiment in that it includes a diaphragm 220 and a movable portion 221. A first plate 291 differs from the first plate 191 in shape. The other respects are the same and are not described here.

The valve 201 constitutes a check valve 260 and an exhaust valve 270. The check valve 260 includes the movable portion 221 and a valve seat 238 positioned around the first vent hole 111 in the first plate 291. In the check valve 260, the movable portion 221 comes into contact with or becomes separated from the valve seat 238 on the basis of the pressure of a first valve chamber 231 and that of a second valve chamber 232.

Next, the exhaust valve 270 includes the diaphragm 220 and the valve seat 139 positioned around the exhaust channel 114. In the exhaust valve 270, the diaphragm 220 comes into contact with or becomes separated from the valve seat 139 on the basis of the pressure of the first valve chamber 231 and that of the second valve chamber 232.

Next, operations of the gas control device 200 during a blood pressure measurement are described.

Figure 8:
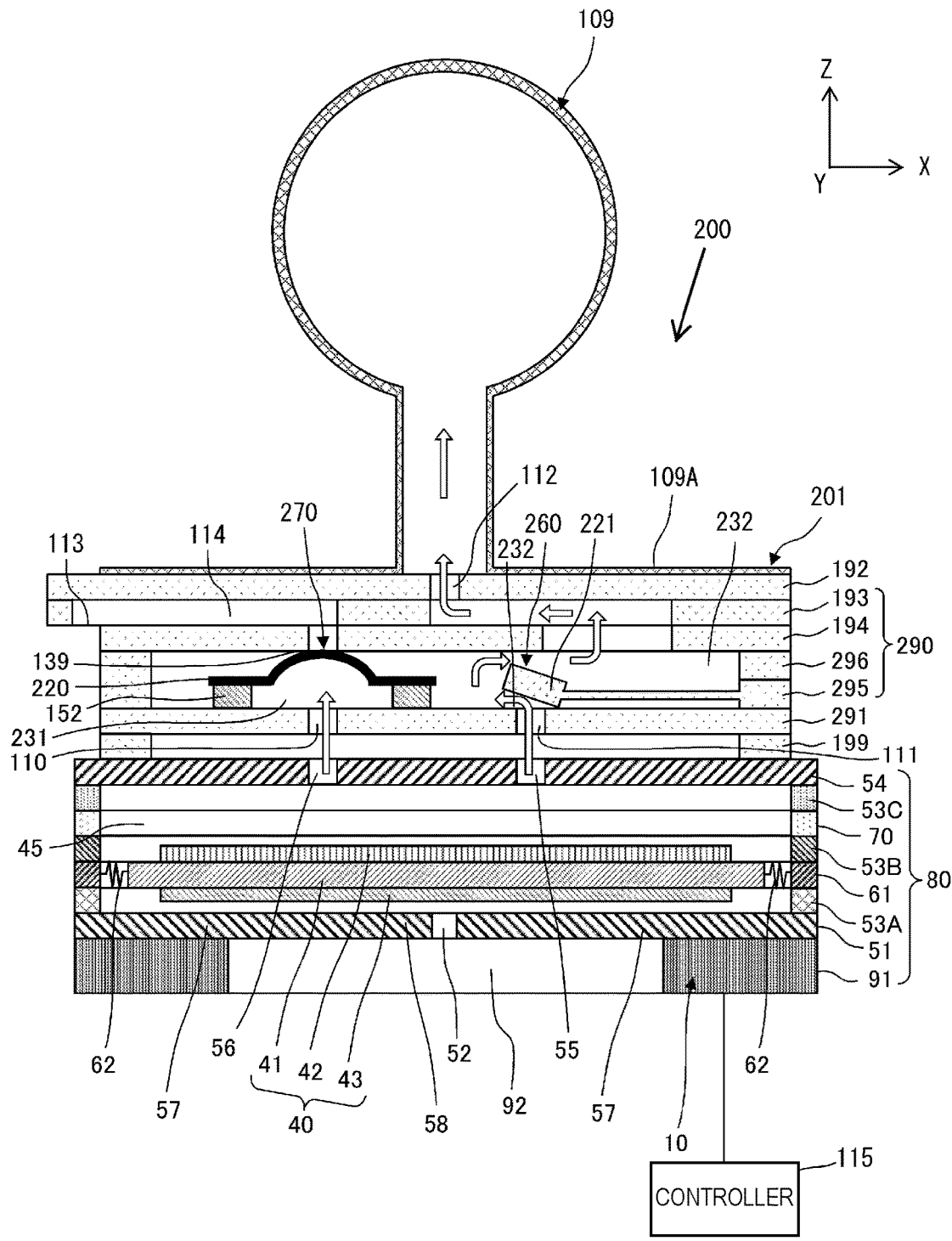
FIG. 8 is a schematic diagram that illustrates an air stream in the gas control device 200 while the pump 10 illustrated in FIG. 6 is driven.

FIG. 8 is a schematic diagram that illustrates an air stream in the gas control device 200 while the pump 10 illustrated in FIG. 6 is driven. The controller 115 activates the pump 10 at the time of starting a blood pressure measurement. When the pump 10 is driven, first, air flows through the cavity 92 and suction hole 52 into the pump chamber 45 in the pump 10. Then, the air is discharged through the discharge hole 55 and discharge hole 56 and flows into the first valve chamber 231 in the valve 201.

In the exhaust valve 270, the pressure of the first valve chamber 231 becomes higher than that of the second valve chamber 232. Thus, as illustrated in FIG. 8, the diaphragm 220 seals the exhaust channel 114 and interrupts the linkage between the second vent hole 112 and exhaust channel 114. In the check valve 260, the pressure of the first vent hole 111 becomes higher than that of the second valve chamber 232. Thus, the movable portion 221 becomes separated from the valve seat 238, and the first vent hole 111 and second vent hole 112 become linked to each other.

Accordingly, air is sent from the pump 10 to the cuff 109 through the first vent hole 111 and second vent hole 112 in the valve 201 (see FIG. 8), and the pressure (air pressure) inside the cuff 109 increases. While the pump 10 is driven, the temperature of the pump 10 keeps rising because of self-heating.

The air moving through the first vent hole 111 and out of the movable portion 221 in the valve 201 flows into the second valve chamber 232 with a pressure slightly lower than the discharge pressure of the pump 10. The discharge pressure of the pump 10 is placed on the first valve chamber 231.

Accordingly, in the valve 201, the pressure of the first valve chamber 231 becomes slightly higher than that of the second valve chamber 232, and the state in which the diaphragm 220 seals the exhaust channel 114 and the movable portion 221 is opened is maintained.

Figure 9:
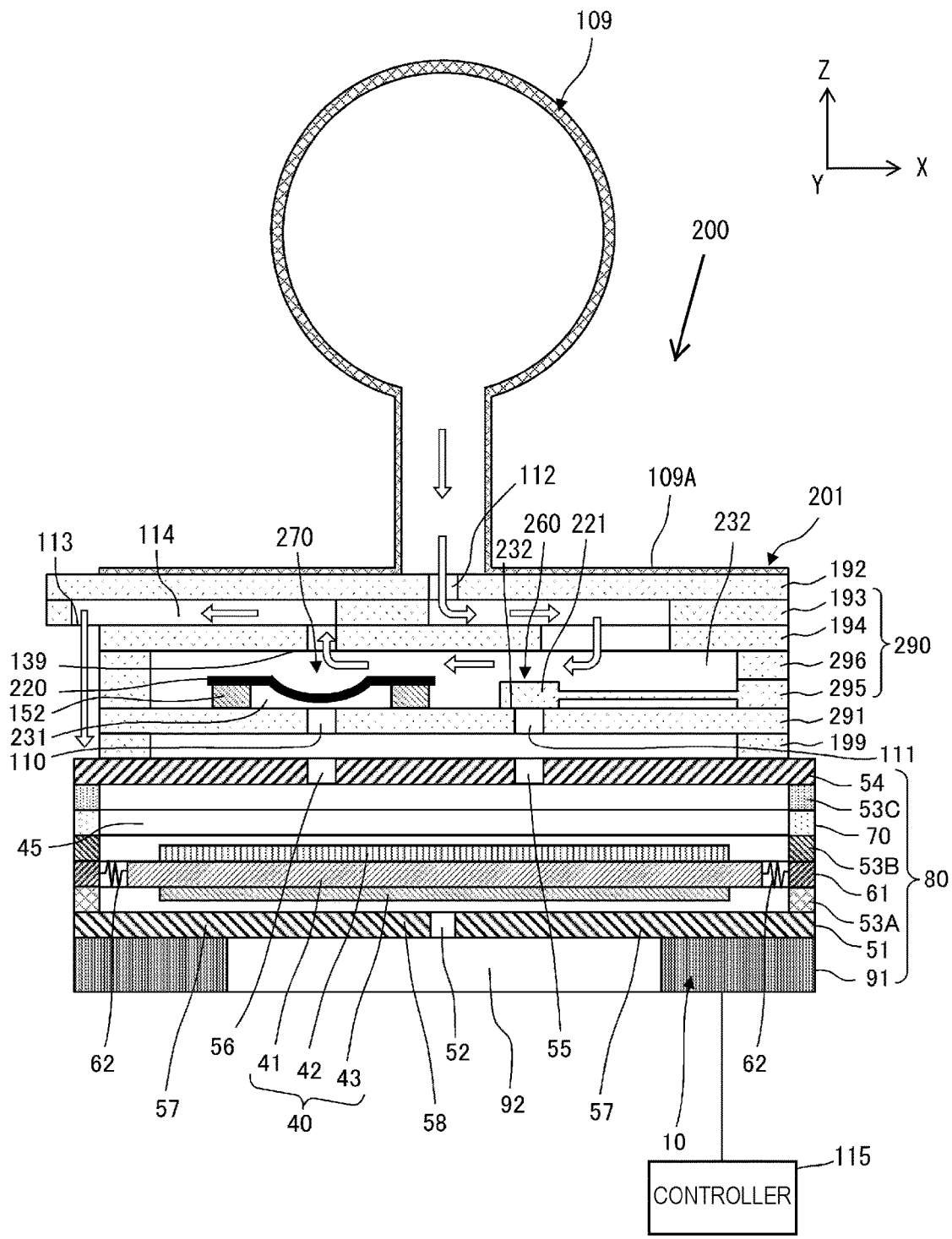
FIG. 9 is a schematic diagram that illustrates an air stream in the gas control device 200 immediately after the pump 10 illustrated in FIG. 6 stops being driven.

FIG. 9 is a schematic diagram that illustrates an air stream in the gas control device 200 immediately after the pump 10 illustrated in FIG. 6 stops being driven. When the blood pressure measurement ends, the controller 115 deactivates the pump 10. When the driving of the pump 10 stops, the air is promptly ejected from the pump chamber 45 and first valve chamber 231 to outside the gas control device 200 through the suction hole 52 and cavity 92 in the pump 10. The pressure of the cuff 109 is placed on the second valve chamber 232 through the second vent hole 112 interposed therebetween.

Accordingly, in the check valve 260, the pressure of the first valve chamber 231 becomes lower than that of the second valve chamber 232. The movable portion 221 seals the first vent hole 111.

In the exhaust valve 270, the pressure of the first valve chamber 231 becomes lower than that of the second valve chamber 232. The diaphragm 220 becomes separated from the valve seat 139 and opens the exhaust channel 114. That is, in the valve 201, the second vent hole 112 and exhaust channel 114 become linked to each other with the second valve chamber 232 interposed therebetween. Thus, the air inside the cuff 109 moves through the second vent hole 112, second valve chamber 232, and exhaust channel 114 and is quickly ejected from the exhaust hole 113 toward the pump housing 80. The volume of the air held in the cuff 109 is significantly higher than that of the pump 10, and a large amount of air is ejected from the exhaust hole 113 toward the pump housing 80.

Consequently, the gas control device 200 can cool the pump housing 80 without a dedicated heat sink or dedicated cooler and can suppress a temperature rise in the pump 10. Therefore, the gas control device 200 can cool the pump 10 without using a cooler even with a low-profile structure.

After that, the controller 115 activates the pump 10 at the time of starting a blood pressure measurement and deactivates the pump 10 when the blood pressure measurement ends. In this manner, for multiple blood pressure measurements, the gas control device 200 can cool the pump 10 every time a blood pressure measurement ends.

As in the case of the first embodiment, the exhaust hole 113 in the above-described configuration is opened from the exhaust channel forming plate 193 to the side near the intermediate plate 194 and is not opened in the surface of the second plate 192. Thus, the second plate 192 can have a wide joining area. The joining area is an area for joining the manchette rubber tube 109A in the cuff 109.

Next, a gas control device according to a third embodiment of the present disclosure is described.

Figure 10A:
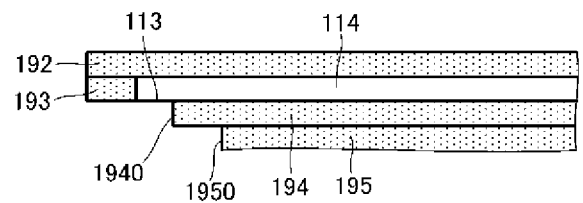
FIG. 10A is an enlarged side cross-sectional view that illustrates a peripheral region of an exhaust hole in a valve according to a third embodiment.
Figure 10B:
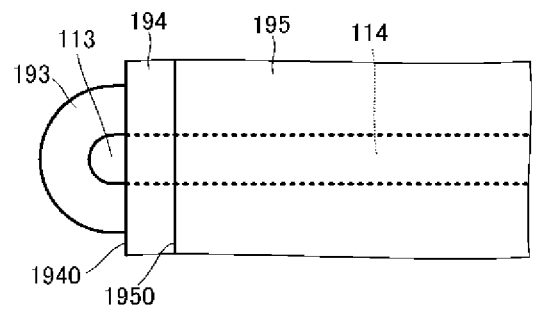
FIG. 10B is an enlarged plan view that illustrates the peripheral region of the exhaust hole in the valve according to the third embodiment.

FIG. 10A is an enlarged side cross-sectional view that illustrates a peripheral region of an exhaust hole in a valve according to the third embodiment. FIG. 10B is an enlarged plan view that illustrates the peripheral region of the exhaust hole in the valve according to the third embodiment. FIG. 10B is a plan view seen from the side near the first plate, that is, the side near the pump.

The gas control device according to the third embodiment differs from that according to the first embodiment in the structure of the peripheral region of the exhaust hole in the valve. The other configuration of the gas control device according to the third embodiment is substantially the same as that of the gas control device according to the first embodiment, and the description about similar points is omitted.

As illustrated in FIGS. 10A and 10B, the exhaust hole 113 is positioned in a first end of the slit in the exhaust channel forming plate 193 and is formed of a portion of the slit that is not covered with the intermediate plate 194. That is, the exhaust hole 113 is a region protruding from the outer edge of the intermediate plate in the exhaust channel 114 and is in contact with a side surface 1940 of the intermediate plate 194.

The frame plate 195 is arranged in a position inward from the intermediate plate 194 in a surface defining the exhaust hole 113 in the channel forming portion 190. In other words, the frame plate 195 is arranged in a position inward from the intermediate plate 194 in a side surface in which the exhaust hole 113 is disposed. That is, in plan view, a side surface 1950 of the frame plate 195 is nearer the center of the channel forming portion 190 than the side surface 1940 of the intermediate plate 194. In other words, the side surface 1950 of the frame plate 195 is in a position set back with respect to the side surface 1940 of the intermediate plate 194.

Thus, the exhaust hole 113 and the side surface 1950, which is nearest the exhaust hole 113 in the frame plate 195, are separated from each other. Accordingly, the surface of the intermediate plate 194 is present between the end surface of the joint surface between the frame plate 195 and intermediate plate 194, that is, the side surface 1950 and the exhaust hole 113.

In such a configuration, in the case where the intermediate plate 194 and frame plate 195 are joined together with an adhesive, if the adhesive is squeezed out from the side surface 1950 of the frame plate 195, it remains on the exposed surface to the frame plate 195 of the intermediate plate 194. Accordingly, blocking of the exhaust hole 113 by the adhesive flowing to the exhaust hole 113 can be suppressed.

Next, a gas control device according to a fourth embodiment of the present disclosure is described.

Figure 11:
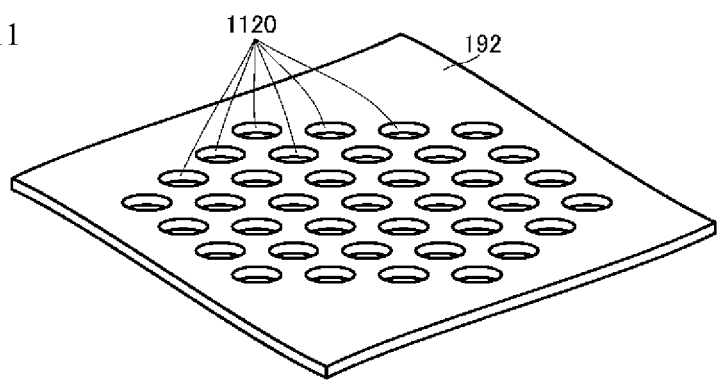
FIG. 11 is an enlarged perspective view that illustrates a section of a first principal surface (outer surface) of a second plate in a gas control device according to a fourth embodiment.
Figure 12A:
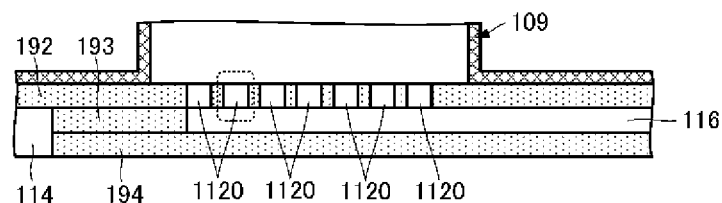
FIG. 12A is a partial cross-sectional view that illustrates a shape of the vicinity of a second vent hole in the gas control device according to the fourth embodiment.
Figure 12B:
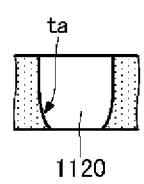
FIG. 12B is a side cross-sectional view of a through hole constituting the second vent hole.
Figure 12C:
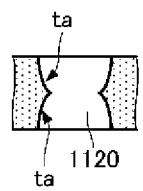
FIG. 12C is a side cross-sectional view of a through hole constituting the second vent hole.

FIG. 11 is an enlarged perspective view that illustrates a section of a first principal surface (outer surface) of a second plate in the gas control device according to the fourth embodiment. FIG. 12A is a partial cross-sectional view that illustrates a shape of the vicinity of a second vent hole in the gas control device according to the fourth embodiment. FIGS. 12B and 12C are side cross-sectional views of through holes constituting the second vent hole.

The gas control device according to the fourth embodiment differs from that according to the first embodiment in the shape of the second vent hole in the valve. The other configuration of the gas control device according to the fourth embodiment is substantially the same as that of the gas control device according to the first embodiment, and the description about similar points is omitted.

As illustrated in FIG. 11, the second plate 192 has a plurality of through holes 1120. The plurality of through holes 1120 constitute the second vent hole.

The plurality of through holes 1120 have substantially the same shapes. One example shape may be circular in plan view. The opening area of each of the plurality of through holes 1120 as seen in plan view is smaller than the opening area of the second vent hole illustrated in the first embodiment. For example, the opening area of each of the plurality of through holes 1120 is smaller than the size of typical foreign matter arising inside the cuff 109, for example, a fragment of a material forming the cuff 109 or the like.

Thus, if foreign matter arises inside the cuff 109, the entry of the foreign matter into the second valve chamber 132 in the valve 101 can be suppressed. Moreover, the occurrence in which the foreign matter becomes caught between the opening near the second valve chamber 132 in the exhaust channel 114, that is, the valve seat 139 and the diaphragm 120 can be suppressed.

Accordingly, the fault of failing to fully cover the opened portion near the second valve chamber 132 in the exhaust channel 114 with the diaphragm 120 can be suppressed, and the occurrence of faults of the pump can be suppressed.

The sum of the opening areas of the plurality of through holes 1120 may preferably be equal to or larger than the opening area of the second vent hole 112. Thus, even when the opening area of each of the plurality of through holes 1120 is small, a bottleneck in a gas flow caused by the plurality of through holes 1120 can be suppressed.

Furthermore, as illustrated in FIGS. 12B and 12C, each of the plurality of through holes 1120 may preferably have a tapered shape ta, which has a portion that gradually reduces its opening area from the first principal surface (outer surface) toward the second principal surface (surface near the channel forming portion 190) of the second plate 192. In this case, foreign matter from the cuff 109 side is more difficult to enter the second valve chamber 132.

The opening area of each of the plurality of through holes 1120 may preferably be smaller than a minimum area of the second channel. The minimum area of the second channel indicates the smallest cross-sectional area at any location of the second channel.

Thus, if foreign matter arises inside the cuff 109 and passes through the through holes 1120, the foreign matter can be prevented from blocking the second channel, which includes the exhaust channel 114.

Next, a gas control device according to a fifth embodiment of the present disclosure is described.

Figure 13A:
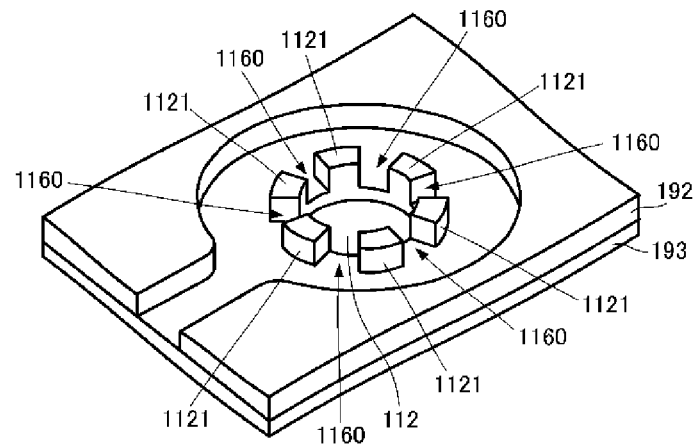
FIG. 13A is an enlarged perspective view that illustrates a section of a first principal surface (outer surface) of a second plate in a gas control device according to a fifth embodiment.
Figure 13B:
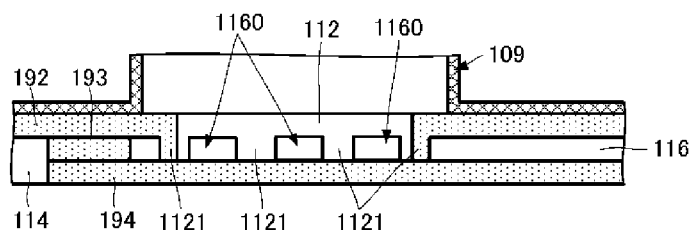
FIG. 13B is a partial cross-sectional view that illustrates a shape of the vicinity of a second vent hole in the gas control device according to the fifth embodiment.

FIG. 13A is an enlarged perspective view that illustrates a section of a first principal surface (outer surface) of a second plate in the gas control device according to the fifth embodiment. FIG. 13A illustrates a state where the first principal surface (outer surface) of the second plate is on the bottom side. FIG. 13B is a partial cross-sectional view that illustrates a shape of the vicinity of a second vent hole in the gas control device according to the fifth embodiment.

The gas control device according to the fifth embodiment differs from that according to the first embodiment in the shape of the vicinity of the second vent hole in the valve. The other configuration of the gas control device according to the fifth embodiment is substantially the same as that of the gas control device according to the first embodiment, and the description about similar points is omitted.

As illustrated in FIGS. 13(A) and 13(B), the exhaust channel forming plate 193 has a communication hole 116. The communication hole 116 is formed of a slit in the exhaust channel forming plate 193. A first end of the communication hole 116 overlaps the second vent hole 112 in plan view and communicates with the second vent hole 112. Although not illustrated, a second end of the communication hole 116 communicates with the second valve chamber 132.

The first end of the communication hole 116 is an opened portion that is circular in plan view, and the opened portion overlaps the second vent hole 112.

A plurality of protrusions 1121 are arranged on the side near the exhaust channel forming plate 193 (side near the second principal surface) in the second plate 192. The plurality of protrusions 1121 are arranged at predetermined intervals so as to surround the perimeter of the second vent hole 112. The intervals are set on the basis of the size of foreign matter arising from the cuff 109.

The height of each of the plurality of protrusions 1121 is approximately equal to that of the exhaust channel forming plate 193. Accordingly, the end of each of the protrusions 1121 is in contact with the intermediate plate 194. Thus, a plurality of holes 1160 surrounded by the plurality of protrusions 1121, second plate 192, and intermediate plate 194 are disposed between the second valve chamber 132 and second vent hole 112. The opening area of each of the plurality of holes 1160 is smaller than the size of foreign matter arising from the cuff 109.

In this configuration, as in the case of the gas control device according to the fourth embodiment, if foreign matter arises inside the cuff 109, the entry of the foreign matter into the second valve chamber 132 in the valve 101 can be suppressed. Accordingly, imperfect covering of the opened portion of the exhaust channel 114 near the second valve chamber 132 by the diaphragm 120 can be suppressed, and the occurrence of faults of the pump can be suppressed.

In addition, the sum of the opening areas of the plurality of holes 1160 may preferably be equal to or larger than the opening area of the second vent hole 112. Thus, even when the opening area of each of the plurality of through holes 1160 is small, limiting a gas flow by the plurality of through holes 1160 can be suppressed.

The end of each of the plurality of protrusions 1121 may not be in contact with the intermediate plate 194. The height of the gap between the protrusion 1121 and intermediate plate 194 is smaller than the size of foreign matter in the cuff 109. Thus, substantially the same advantages as those described above are obtainable. The plurality of protrusions can be arranged in any positions between the end portion of the communication hole 116 communicating with the second vent hole 112 and the end portion communicating with the second valve chamber 132.

Next, a derivative example of the gas control device in the present disclosure is described.

Figure 14:
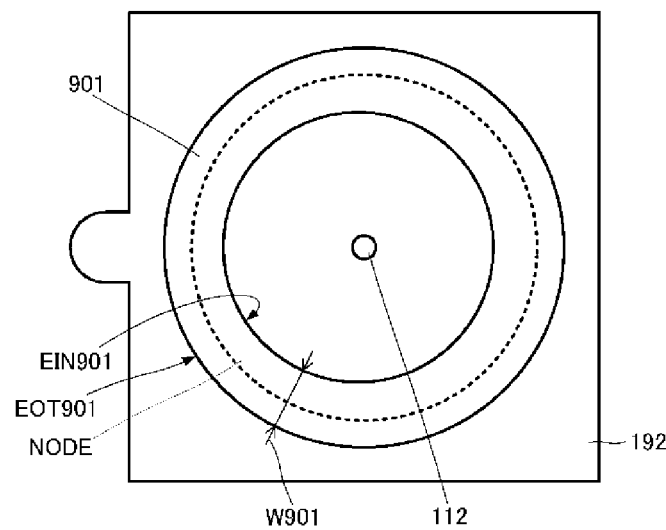
FIG. 14 is a plan view that schematically illustrates a node region in the valve in the gas control device.

FIG. 14 is a plan view that schematically illustrates a node region in the valve in the gas control device.

As illustrated in FIG. 14, a node region 901 is a region including a node NODE of vibration of the second plate 192 caused by driving of the pump. The vibration of the second plate 192 propagates in a direction in which it concentrically spreads, and the node NODE occurs on the way in this propagation direction. Accordingly, the node NODE is circular. By being joined to the second plate 192 at the first principal surface including the node region 901, the cuff 109 can be stably joined to the second plate 192.

The node region 901 changes depending on the planer shape of the second plate 192. For example, because the node NODE occurs in the position of a×R (a is a constant), where R is the distance from the center point (position of the second vent hole 112) to a corner when the planar shape is a regular polygon and R is the radius when it is a circle, the joint portion 901 may be arranged in a position including the node NODE. Specifically, for a square, a is 0.53; for a regular hexahedron, a is 0.61; for a regular octagon, a is 0.64; for a regular decagon, a is 0.65; for a circle, a is 0.67.

Accordingly, the valve 201 and gas control device 200 can achieve a reduction in profile and can have a wide joining area.

OTHER EMBODIMENTS

In the above-described embodiments, air is used as gas. The present disclosure is not limited to this configuration. In practice, the present disclosure is also applicable to the use of gas other than air.

The pump 10 in the above-described embodiments includes the piezoelectric actuator 40 bending and vibrating in a unimorph structure. The present disclosure is not limited to this configuration. The pump may include an actuator that bends and vibrates in a bimorph structure, which includes a vibration plate and piezoelectric elements attached on both surfaces of the vibrating plate.

The pump 10 in the above-described embodiments includes the piezoelectric actuator 40, which bends and vibrates by contraction and expansion of the piezoelectric element 42. The present disclosure is not limited to this configuration. For example, the pump may include an actuator that bends and vibrates by electromagnetic driving.

The pump 10 in the above-described embodiments includes the discharge holes 55 and 56. The present disclosure is not limited to this configuration. For example, the pump 10 may include either one of the discharge holes 55 and 56.

The piezoelectric element in the above-described embodiments is made of a PZT-based ceramic material. The present disclosure is not limited to this configuration. For example, the piezoelectric element may be made of other piezoelectric materials, including a lead-free based piezoelectric ceramic material, such as a potassium-sodium niobate-based or alkali niobate-based ceramic material.

The valve 101 in the above-described embodiments includes the first vent holes 110 and 111. The present disclosure is not limited to this configuration. For example, the valve 101 may include either one of the first vent holes 110 and 111.

The opening of the exhaust hole 113 in the above-described embodiments is oriented in the Z-axis direction, that is, faces the pump 10. The present disclosure is not limited to this configuration. For example, the opening of the exhaust hole 113 may be oriented in the X-axis direction.

Pumps usable in the above-described embodiments are not limited to the above-described pump 10. For example, in place of the pump 10, a pump illustrated in FIG. 2 in Japanese Patent Application No. 2011-244053 or other pumps may be used.

Lastly, the description about the above embodiments is illustrative in all respects and is not restrictive. The scope of the present disclosure is indicated by not the above-described embodiments but the scope of the claims. The scope of the present disclosure includes a scope equivalent to the scope of the claims.

10 pump, 40 piezoelectric actuator, 41 vibration plate, 42 piezoelectric element, 45 pump chamber, 52 suction hole, 55, 56 discharge hole, 60 vibration plate unit, 61 frame plate, 62 coupling portion, 80 pump housing, 100, 200 gas control device, 101 valve, 109 cuff, 109A manchette rubber tube, 110, 111 first vent hole, 112 second vent hole, 113 exhaust hole, 114 exhaust channel, 115 controller, 120 diaphragm, 121 hole portion, 131 first valve chamber, 132 second valve chamber, 138 valve seat, 138A, 138B protrusion portion, 139 valve seat, 152 sealing member, 160 check valve, 170 exhaust valve, 190 channel forming plate, 191, 291 first plate, 192 second plate, 201 valve, 220 diaphragm, 221 movable portion, 231 first valve chamber, 232 second valve chamber, 238 valve seat, 260 check valve, 270 exhaust valve, 290 channel forming plate, 295 non-return plate, 296 frame plate, 901 node region, 1120, 1160 through hole, 1121 protrusion, 1940 side surface of intermediate plate 194, 1950 side surface of frame plate 195

The invention claimed is:

1. A valve comprising:
    a first plate having a first vent hole;
    a second plate having a second vent hole;
    a diaphragm between the first plate and the second plate;
    a channel forming plate having an exhaust hole and comprising an intermediate plate and an exhaust channel forming plate, the intermediate plate, the exhaust channel forming plate, and the second plate being laminated such that the exhaust channel forming plate is between the intermediate plate and the second plate;
    a first channel connecting the first vent hole and the second vent hole;
    a second channel connecting the second vent hole and the exhaust hole; and
    a valve member forming a first valve chamber within the first channel between the first plate and the channel forming plate, and forming a second valve chamber within the second channel between the second plate and the channel forming plate, the valve member connecting the first channel and interrupting the second channel, or interrupting the first channel and connecting the second channel, based on a pressure of the first valve chamber and a pressure of the second valve chamber,
    wherein the second channel comprises a laterally extending exhaust channel portion connecting the second valve chamber to the exhaust hole,
    wherein a perimeter of the diaphragm is smaller than a perimeter of the first plate and is smaller than a perimeter of the second plate, and
    wherein a whole of the diaphragm is within the first valve chamber and the second valve chamber.

2. The valve according to claim 1, wherein the valve member:
    connects the first channel and interrupts the second channel when the pressure of the first valve chamber is equal to or greater than the pressure of the second valve chamber, and
    interrupts the first channel and connects the second channel when the pressure of the first valve chamber is less than the pressure of the second valve chamber.

3. The valve according to claim 1, wherein the exhaust channel forming plate forms the laterally extending exhaust channel portion between the second plate and the intermediate plate.

4. The valve according to claim 1, wherein a material of each of the first plate, the second plate, and the channel forming plate is a metal.

5. A gas control device comprising:
    the valve according to claim 1;
    a pump having a discharge hole connected to the first vent hole; and
    a container connected to the second vent hole,
    wherein the exhaust hole is open to the atmosphere.

6. The gas control device according to claim 5, wherein the exhaust hole opens exterior to the container.

7. The gas control device according to claim 5, wherein an opening of the exhaust hole faces an outside wall of the pump.

8. The gas control device according to claim 5, wherein the pump has a suction hole, and the suction hole is always in communication with the discharge hole.

9. A sphygmomanometer comprising:
the gas control device according to claim 5.

10. The valve according to claim 1, wherein the laterally extending exhaust channel portion extends laterally beyond the first valve chamber or the second valve chamber.

11. The valve according to claim 1, further comprising an exhaust valve that connects the second valve chamber to the laterally extending exhaust channel portion.

12. The valve according to claim 1, wherein an exterior surface of the second plate is flat.

13. The valve according to claim 1, wherein the exhaust channel forming plate forms a laterally extending exhaust channel portion of the second channel between the second plate and the intermediate plate, the laterally extending exhaust channel portion extending laterally beyond the first valve chamber or the second valve chamber.

14. A valve comprising:
a first plate having a first vent hole;
a second plate having a second vent hole;
a diaphragm between the first plate and the second plate;
a channel forming plate having an exhaust hole and comprising an intermediate plate and an exhaust channel forming plate, the intermediate plate, the exhaust channel forming plate, and the second plate being laminated such that the exhaust channel forming plate is between the intermediate plate and the second plate;
a first channel connecting the first vent hole and the second vent hole;
a second channel connecting the second vent hole and the exhaust hole; and
a valve member forming a first valve chamber within the first channel between the first plate and the channel forming plate, and forming a second valve chamber within the second channel between the second plate and the channel forming plate, the valve member connecting the first channel and interrupting the second channel, or interrupting the first channel and connecting the second channel, based on a pressure of the first valve chamber and a pressure of the second valve chamber,
wherein an exterior surface of the second plate is flat,
wherein a perimeter of the diaphragm is smaller than a perimeter of the first plate and is smaller than a perimeter of the second plate, and
wherein a whole of the diaphragm is within the first valve chamber and second valve chamber.

15. The valve according to claim 14, wherein the valve member:
connects the first channel and interrupts the second channel when the pressure of the first valve chamber is equal to or greater than the pressure of the second valve chamber, and
interrupts the first channel and connects the second channel when the pressure of the first valve chamber is less than the pressure of the second valve chamber.

16. The valve according to claim 14, wherein a material of each of the first plate, the second plate, and the channel forming plate is a metal.

17. A gas control device comprising:
the valve according to claim 14;
a pump having a discharge hole connected to the first vent hole; and
a container connected to the second vent hole,
wherein the exhaust hole is open to the atmosphere.

18. The gas control device according to claim 17, wherein the exhaust hole opens exterior to the container.

19. The gas control device according to claim 17, wherein an opening of the exhaust hole faces an outside wall of the pump.

20. A sphygmomanometer comprising:
the gas control device according to claim 17.

* * * * *